(12) United States Patent
Asomani

(10) Patent No.: US 7,261,691 B1
(45) Date of Patent: Aug. 28, 2007

(54) PERSONALIZED EMERGENCY MEDICAL MONITORING AND TRANSMISSION SYSTEM

(76) Inventor: Kwabena Asomani, 9716 Indian Princess Dr., Ft. Washington, MD (US) 20744

(*) Notice: Subject to any disclaimer, the term of this patent is extended or adjusted under 35 U.S.C. 154(b) by 0 days.

(21) Appl. No.: 10/902,844

(22) Filed: Aug. 2, 2004

(51) Int. Cl.
A61B 5/00 (2006.01)

(52) U.S. Cl. .................. 600/300; 600/301; 600/347; 128/920; 340/573.1

(58) Field of Classification Search ........ 600/300–301, 600/345, 347, 361, 365; 128/903–905, 920–925, 128/897; 340/539.1, 573.1
See application file for complete search history.

(56) References Cited

U.S. PATENT DOCUMENTS

| | | | |
|---|---|---|---|
| 5,919,141 A | 7/1999 | Money et al. | |
| 6,302,844 B1 * | 10/2001 | Walker et al. | 600/300 |
| 6,402,708 B1 | 6/2002 | Sitte | |
| 6,572,542 B1 * | 6/2003 | Houben et al. | 600/300 |
| 6,579,231 B1 * | 6/2003 | Phipps | 600/300 |
| 2001/0036832 A1 | 11/2001 | McKay | |
| 2002/0116080 A1 | 8/2002 | Birnbach et al. | |
| 2002/0145522 A1 | 10/2002 | Pembroke | |

OTHER PUBLICATIONS

Glucowatch G2 Automatic Glucose Biographer "User's Guide".

* cited by examiner

Primary Examiner—Max F. Hindenburg
Assistant Examiner—Michael C Astorino
(74) Attorney, Agent, or Firm—McIntyre Harbin & King

(57) ABSTRACT

A portable emergency medical monitoring and transmission system capable of sending a message to a personal caretaker and/or an emergency response center. The system includes a wearable monitor/transmitter device including a glucose level detector, a geolocation system, and a communication interface to send and/or receive a message. A processor operable within the device collects information produced by the glucose level detector and the geolocation system to determine whereabouts and existence of a hypoglycemic or hyperglycemic condition of the patient. Upon detecting an unsafe medication condition, the processor assembles a message that includes patient identifier data, whereabouts of said patient, and an emergency alert indication; and activates a transmitter to transmit an emergency message in response to a hypoglycemic or hyperglycemic condition. An optional caretaker receiver receives the message and produces a local alarm indicating that the patient requires assistance. A transmission path of the transmitter conveys, in response to an emergency alert indication, the emergency message to an emergency response center indicating that the patient needs help.

22 Claims, 7 Drawing Sheets

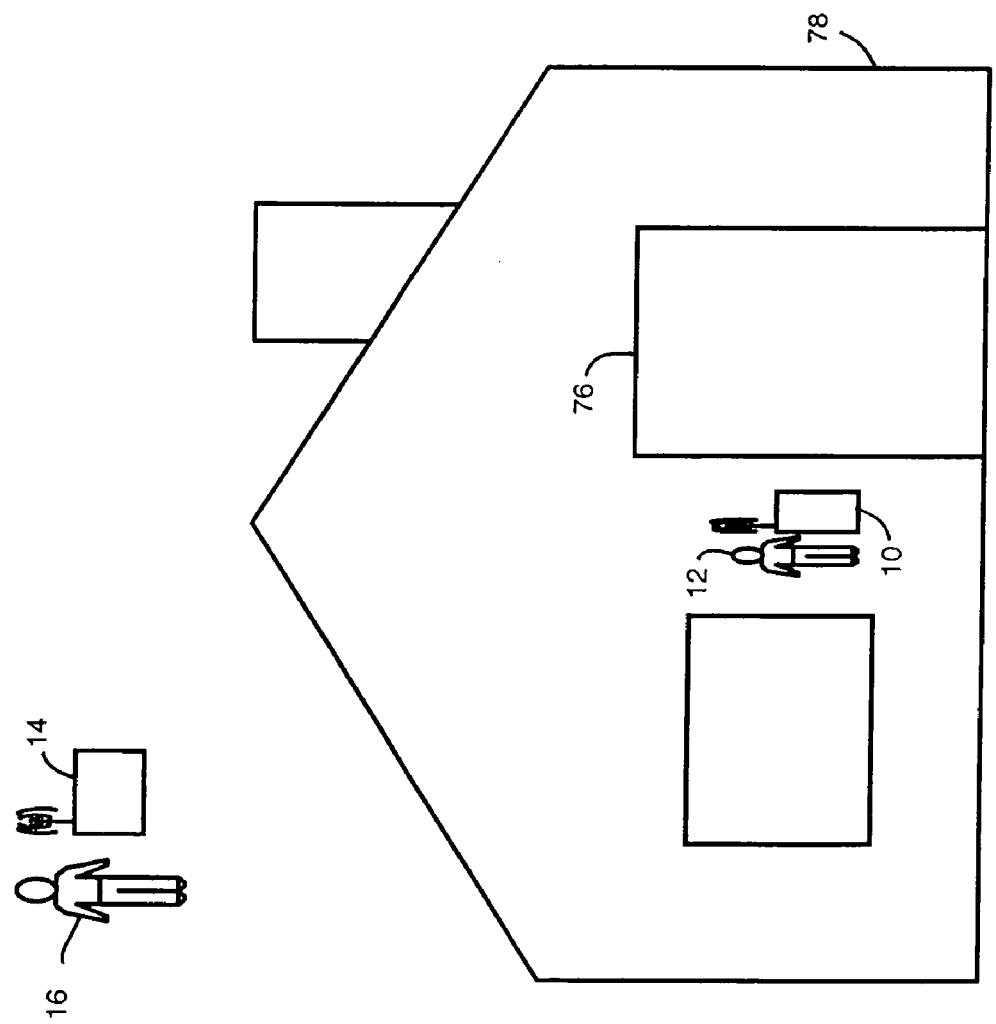
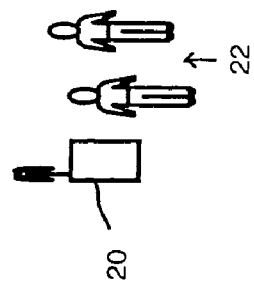
FIG. 5

PERSONALIZED EMERGENCY MEDICAL MONITORING AND TRANSMISSION SYSTEM

CROSS-REFERENCE TO RELATED APPLICATION

This invention claims the benefit of U.S. patent application Ser. No. 10/736,105 filed Dec. 11, 2003 entitled Glucose Locator Transmitter.

BACKGROUND

This invention relates to an emergency medical monitoring and response system and method, but more specifically, to a wearable device and related support personnel communication equipment to detect an emergency medical condition of diabetic patient and/or to report such condition to a personal caretaker.

Diabetes afflicts a significant portion of the population. The disease affects persons whose bodily functions are unable to maintain a proper blood glucose level without medication, diet or treatment. An insulin injection is common treatment when glucose levels rise when bodily functions fail to produce sufficient insulin while sugar consumption treats low blood glucose levels. If an unsafe blood glucose condition remains untreated—even for a few moments—the patient may lose consciousness, become comatose, suffer irreparable brain damage, and possibly die. As such, persons suffering from diabetes must constantly be monitored and guarded against hypoglycemia or hypoglycemia, which restricts the person's activity and mobility.

Thus, a goal of the present invention is to enable substantially unrestricted mobility of diabetic individual without an undue risk of a lapse in treatment should an emergency condition arise.

It is another goal of the present invention to provide a wearable device that automatically monitors blood glucose levels and to prompt the patient to take appropriate action and, when the patient is unable to perform self-treatment, to transmit an emergency message as to the patient's condition and whereabouts to a personal caretaker and/or emergency medical response center, such as a hospital or an ambulatory service.

It is another goal of the present invention to provide a wearable device, as aforestated, that includes a location detector such as a GPS receiver, and a transceiver, such as a cellular telephone interface, to provide a transmission of the patient's condition, whereabouts, or other information.

It is another goal of the present invention to provide a wearable device that automatically treats a diabetic upon detection of an unsafe blood glucose level should the diabetic fails to implement self-treatment within a predetermined period of time after detection of an unsafe diabetic condition.

SUMMARY OF THE INVENTION

According to a first aspect of the invention, there is provided an emergency medical monitoring and transmission system capable of sending a message to a personal caretaker and/or an emergency response center where the system comprises a wearable monitor/transmitter device including a glucose detector to detect a blood glucose level of a patient, a geolocation system that indicates the patient's location, and a communication interface to send and/or receive an emergency message; and a processor operable with the wearable monitor/transmitter device to collect information produced by the glucose detector and the geolocation system to determine the whereabouts and/or existence of a hypoglycemic or hyperglycemic condition of the patient. The processor further includes program instructions to effect assembly of a message that includes patient identifier data, whereabouts information, and an emergency alert indication. The processor activates the communication interface to transmit the message in response to a hypoglycemic or hyperglycemic condition of the patient. The system optionally includes a caretaker receiver accessible by a personal caretaker of the patient to receive the message and, in response to receipt of said emergency alert indication, to produce an alarm indicating that the patient requires assistance. Further, the system includes a transmission path to send, in response to an emergency alert indication, an emergency message to an emergency response center indicating that the patient requires assistance.

An additional feature of the invention includes the emergency message having patient identifier and whereabouts data embedded therein, and a receiver located at an emergency medical response center to receive the emergency message, to produce an alarm, and to display the patient's condition and whereabouts.

An additional feature of the invention includes the processor having program instructions to produce and record historical trend information indicating past levels of blood glucose.

An additional feature of the invention includes the processor effecting transmission of blood glucose level historical trend information to at least one of the caretaker receiver and the emergency response center.

An additional feature of the invention includes the processor effecting collection of blood glucose levels at time instances that vary according to proximity of a detected level to an unsafe upper or lower limit.

An additional feature of the invention includes a wireless network interface of the system to communicate with a wireless network access point of a facility of the patient, where the message is relayed to the personal caretaker and/or the emergency response center.

An additional feature of the invention includes a panic switch on the unit worn by the patient where a processor thereof responds to activation of the panic switch to effect immediate transmission of an emergency message.

An additional feature of the invention includes a reset switch on the unit worn by the patient where the processor responds to activation of the reset switch to cancel an alarm condition and/or to inhibit transmission of the emergency message.

An additional feature includes an glucose reservoir and glucose pump disposed on the unit worn by the patient where the processor effects automatic administration of glucose from the reservoir through a catheter and into the patient upon a failure of the patient to acknowledge an alarm condition within a predetermined time period, e.g., three to five minutes, more or less. The processor may control the amount of glucose injection to be commensurate with the extent of a sensed hypoglycemic condition, as measured by the glucose level detector.

According to another aspect of the invention, there is provided a portable medical monitoring and transmission system that sends an emergency message to an emergency response center comprising a portable monitor/transmitter device including a glucose level detector to detect a blood glucose level of a patient, a patient position monitor that indicates the location of the patient, and a transmitter to send the emergency message; a processor operable with the portable monitor/transmitter device worn by the patient to effect acquisition of data produced by the glucose level detector and the patient position monitor to determine whereabouts and existence of an unsafe medical condition of the patient, the processor further including program instructions to effect assembly of the emergency message to include patient identifier data, patient position information, and/or an emergency alert indication, and to activate the transmitter to transmit the emergency message in response to the unsafe medical condition; and a transmission path of the transmitter to send, in response to an emergency alert indication, the emergency message to an emergency response center and/or a personal caretaker indicating that the patient requires assistance.

According to another aspect of the invention, a method of sending an alert that a diabetic patient needs assistance comprises the steps of detecting a blood glucose level of the patient to produce blood glucose level information; determining the location of the patient, accessing the blood glucose level information to determine whether the information lies within preset limits corresponding to a hypoglycemic or hyperglycemic condition of the patient; in response to the information lying outside of he preset limits, assembling an emergency message that identifies the patient, the whereabouts of the patient, and an emergency alert indication; and transmitting the emergency message to an emergency response center and/or a personal caretaker of the patient to indicate that the patient requires assistance. The method may additionally comprise inhibiting the transmitting step in response to a cancel alarm signal produced by the patient. Further, the method may additionally comprise automatically injecting glucose into the patient upon a failure to acknowledge the emergency alert indication within a given time period after the glucose monitor detects a hypoglycemic condition, e.g., low blood glucose level.

Other aspects and features of the invention will become apparent upon review of the following detailed description of illustrative embodiments taken in connection with the accompanying drawings. The invention, though, is pointed out with particularity by the appended claims.

BRIEF DESCRIPTION OF THE DRAWINGS

FIG. 5 shows a communication arrangement where the patient is located in a facility that interacts with secure access controls of an emergency response personnel.

DESCRIPTION OF ILLUSTRATIVE EMBODIMENTS

Figure 1:
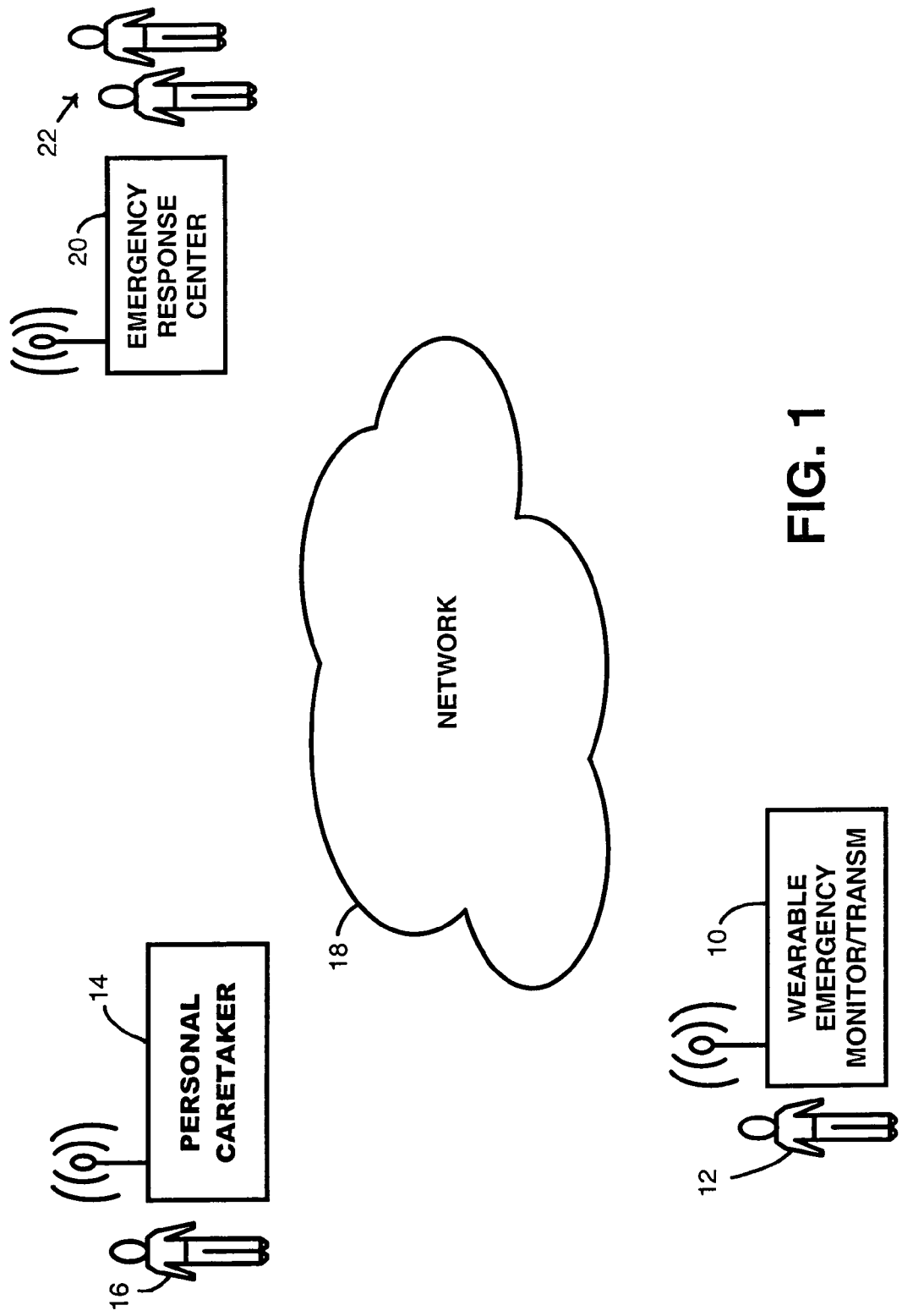
FIG. 1 shows an exemplary communication arrangement among a patient's wearable monitor/transmitter device, a caretaker's receiver, and an emergency response center according to one aspect of the invention.

FIG. 1 shows a personalized emergency medical monitoring and transmission system according to one aspect of the invention. Such a system includes a wearable device 10 of patient 12 that communicates via network 18 with receiver 14 of a personal caretaker 16 (e.g., a relative or family member) and receiver 20 of an emergency response center. Network 20 may comprise wireless network, such as a cellular telephone network, a pager network, a packet data network (Internet or ATM), a local area or wide area network, a combination of one or more of such networks, or any other communication system to convey messages from the patient 12 to emergency response personnel 22 and/or personal caretaker 16.

Wearable transceiver device 10 preferably includes a glucose monitor, such as a GlucoWatch G2 Biographer commercially available from Cygnus, Inc. of Redwood City, Calif., a GPS (global positioning system) module to detect the location of patient 12, and a communication interface and transceiver device such as mobile telephone and interface. Such a GPS module is commercially available from Motorola or Analog Devices (e.g., NAV 2300 navigation chip). The glucose level detector collects and analyzes glucose through the patient's skin, typically at the wrist. Wearable device 10 also includes a special purpose processor interfaced with the GPS module, the glucose level monitor, and a communication interface to effect transmission of an emergency message to the personal caretaker 10 or emergency personnel 22 that identifies the patient, his or her whereabouts, an emergency medical condition, and/or other pertinent information about the patient. Other attributes of wearable device 10 include a display that displays glucose levels, an audible and/or visual local alarm to alert the patient of the onset and/or existence of an unsafe medical condition, a "panic switch" enabling the patient to immediately call for help, and a reset switch to reset the device 10 or cancel an alarm (locally and remote transmission thereof) at the will of the patient. The local alarm may also include a vibrator or buzzer to warn the patient of an unsafe medical condition.

The personal caretaker's receiver device 14 receives messages from the patient's wearable device 10 via network 18. Such messages may include patient identifying information, blood glucose levels, an the patient's whereabouts. Device 14 may also include a transmitter or cellular telephone interface to send messages either to patient 12 or emergency response personnel 22. Device 20 preferably comprises installed communication equipment located at the emergency response center.

Figure 2:
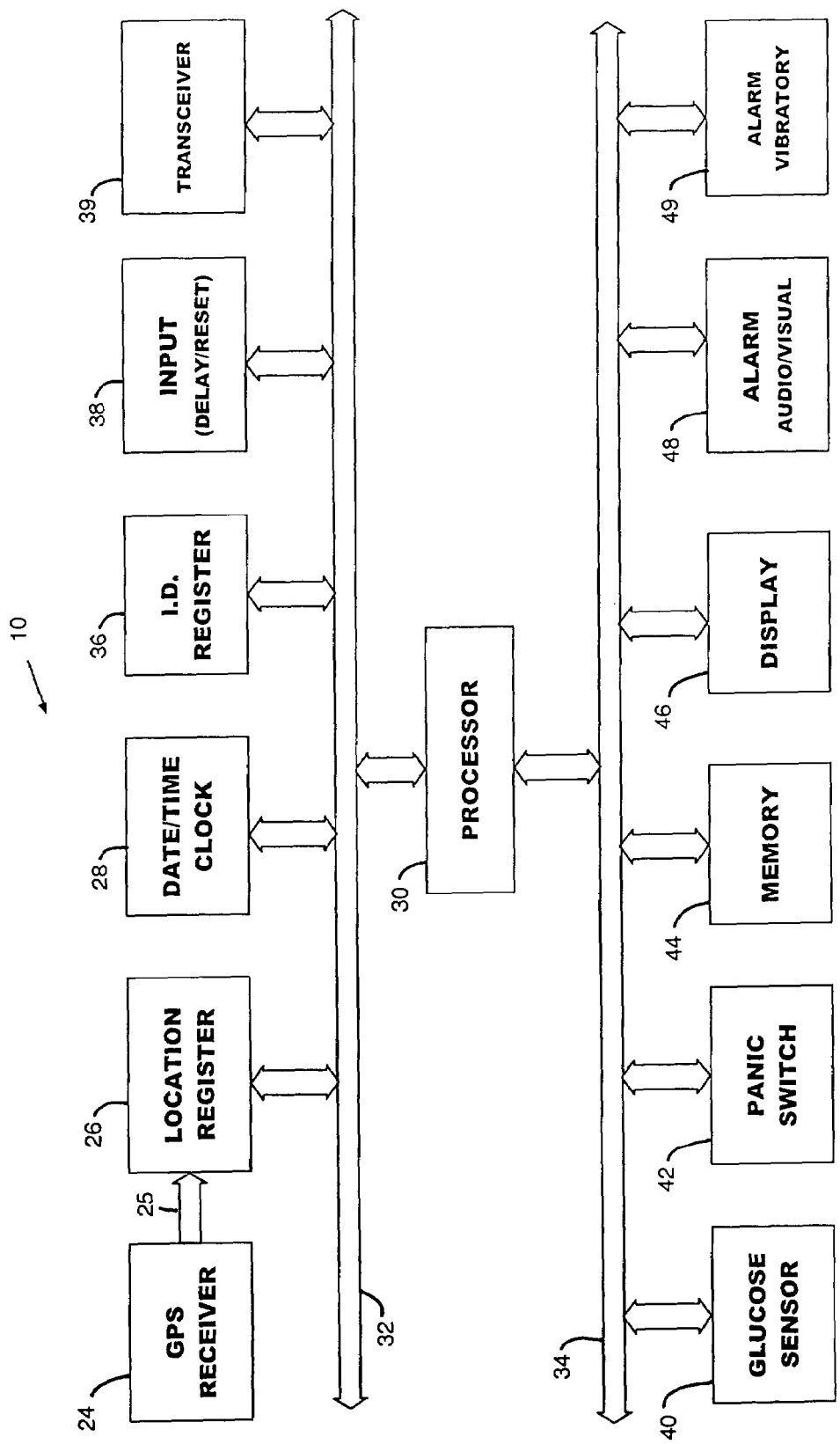
FIG. 2 is an exemplary circuit block diagram of a wearable monitor/transmitter device of FIG. 1 that may be carried or worn by a diabetic person according an aspect of the present invention.

FIG. 2 is a circuit block diagram of an exemplary wearable device 10 having a processor 30 that communicates with various peripheral devices via buses 32 and 34. GPS (global positioning system) receiver 24 detects the location of the patient and supplies coordinates to a location register 26 via bus 25, a date/time clock 28 that enables time-stamping of information collected by processor 30, an identification register 36 that may be preset or manually programmed with patient identifier information, and I/O interface or input 38 to enable resetting of the operation of processor 30 or to delay an event, such as transmitting an emergency message; and a transceiver that emits a signal carrying a message assembled by processor 30.

In practice, data terminals that drive the display of a conventional, off-the-shelf GPS chip may supply the contents of location register 26. Information of date/time clock 28 may also be derived from GPS timing signals. ID register 36 may comprise a unique serial number associated with the patient, or personalized data such as the patient name, medical history, address, emergency contact information, or any other information pertinent to treatment or identity of the patient.

Input 38 may comprise a simple contact switch or a numeric of alphanumeric keypad for entering information into elements of device 10, such as personal patient data; location information; device 10 control information, e.g., reset, cancel emergency, or delay emergency; or any other information. In the case where input 38 comprises a contact switch, processor 30 may serially prompt inputs from the patient in conjunction with voice or text prompts on display 46 in order to enter information into device 10.

Bus 34, which also communicates with processor 30, includes a glucose sensor 40; a panic switch 42 to enable the patient 12 to immediately call for help via an emergency message; a memory 44 that stores information and program instructions associated with processor 30; a display to provide textual information, such as glucose levels, to the patient; an alarm 48 to provide a visual and/or audible alarm to the patient, and optionally, a vibratory alarm 49, which also notifies the patient of an emergency medical condition. Panic switch 42 may comprise a contact switch, closure of which is detected by processor 30 via an interrupt line of the processor. Panic switch 42 may also comprise a voice-activated switch, a speech analyzer to receive and respond to verbal commands, or any other input that can be interpreted by processor 30.

In an exemplary operation, processor 30 effects periodic sampling and/or collecting of glucose levels measured by sensor 40 and compares the same with pre-stored limits to determine whether monitored levels lie within a safe range. A indicated above, glucose detector 40 may comprise an off-the-shelf sensor having data ports feeding a local display. Taps can be made on these data ports to collect glucose measurement data, which is acquired by processor 30. Collected information is time/date stamped using time data produced by local clock source 28 and stored in memory 44.

If processor 30 detects an out-of-limit glucose level, it activates a local alarm giving warning to the patient to implement corrective action. Notification may occur using local alarm 48 or 49. The patient may turn off the local alarm or delay transmission of an emergency message at will, via an input 38. If, after processor 30 detects an unsafe medical condition and the patient fails to reset the device 10 or delay emergency message transmission within a specified time, e.g., thirty to sixty seconds, processor 30 assembles an emergency message and activates transceiver 39 to send the message to either or both the personal caretaker 16 (FIG. 1) and the emergency response personnel 22 (FIG. 1). Transceiver 39 may comprise a cellular telephone interface suitable to dial-in to the emergency response center or to establish an Internet connection to convey the message via the Internet. In addition, transceiver 39 may comprise one of many wireless network interfaces to communication with a network, such as wireless LAN (local area network), WAN (wide area network), or MAN (metropolitan area network) interface. Also, transceiver 39 may simply comprise an RF (radio frequency) transceiver using any part of the spectrum and/or any conventional transmission protocol. Preferably, transceiver 39 has the capability of sending and receiving a message although in some designs, the device 39 may simply comprise a transmitter.

In addition, transceiver 39 may be configured to co-act with a local communication system located at the premises of the patient, such as an existing telephone, a personal computer having Internet access, or wireless access points of a wireless network. In this case, transceiver 39 communicates with the local communication system, which, in turn, relays the message to the personal caretaker or the emergency response center via a network or direct communication link.

Display 46, e.g., a backlighted liquid crystal display panel, provides a visual indication of glucose levels enabling the patient to determine whether to perform self-treatment or whether outside medical assistance is necessary. Moreover, although FIG. 2 shows split buses 32, 34, a single bus may be used in actual practice of the invention.

Figure 3:
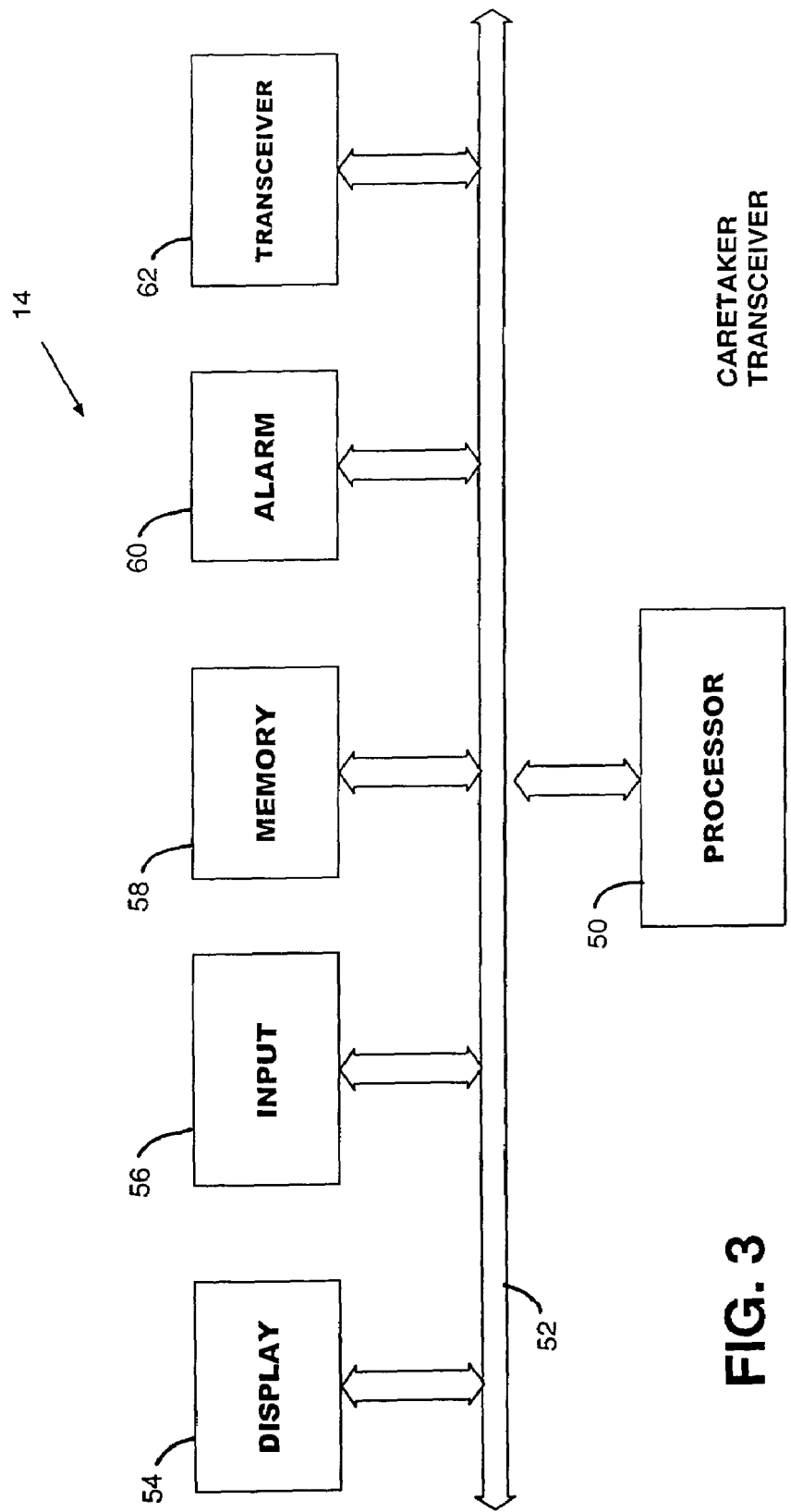
FIG. 3 depicts an exemplary circuit block diagram of a caretaker's device to receive medical status and alert information about the patient according to an aspect of the present invention.

FIG. 3 depicts a circuit block diagram of an exemplary portable unit that is either worn by or remotely available to a personal caretaker of the patient. Personal caretaker unit 14 includes a local processor 50 that communicates with multiple peripheral devices over bus 52. Peripheral elements of unit 14 may operate similar to comparable elements of device 10. Transceiver 62, which may also comprise a cellular telephone interface connected with a cell phone or a wireless LAN (local area network), WAN (wide area network), or MAN (metropolitan area network) interface, receives emergency messages sent by device 10 to enable storage of the same in local memory 58 via control by processor 50. In an alternative arrangement, absent an emergency condition, the wearable patient device 10 may be programmed to periodically send or transmit date- and/or time-stamped blood glucose information so that personal caretaker 16 may monitor a trend of the patient's blood glucose levels or other information via local display 54. Upon receiving an alarm condition sent over network 18 by patient's device 10, processor 50 of the caretaker's unit 14 activates a local alarm 60, which may also comprise an audible, visual, or vibratory alarm to indicate to the personal caretaker that the patient requires or may need assistance. Caretaker device 14 may optionally include the capability to send a message back to the patient indicating that help is on the way, or to the emergency response center to obtain a confirmation that it received the patient's call for help. The personal caretaker may also send other types of information. Such a message may be pre-programmed or derived from information composed by the caretaker using input 56. The emergency response center may send a reply or acknowledgement message to the caretaker's transmission or the patient's call for help.

Figure 4:
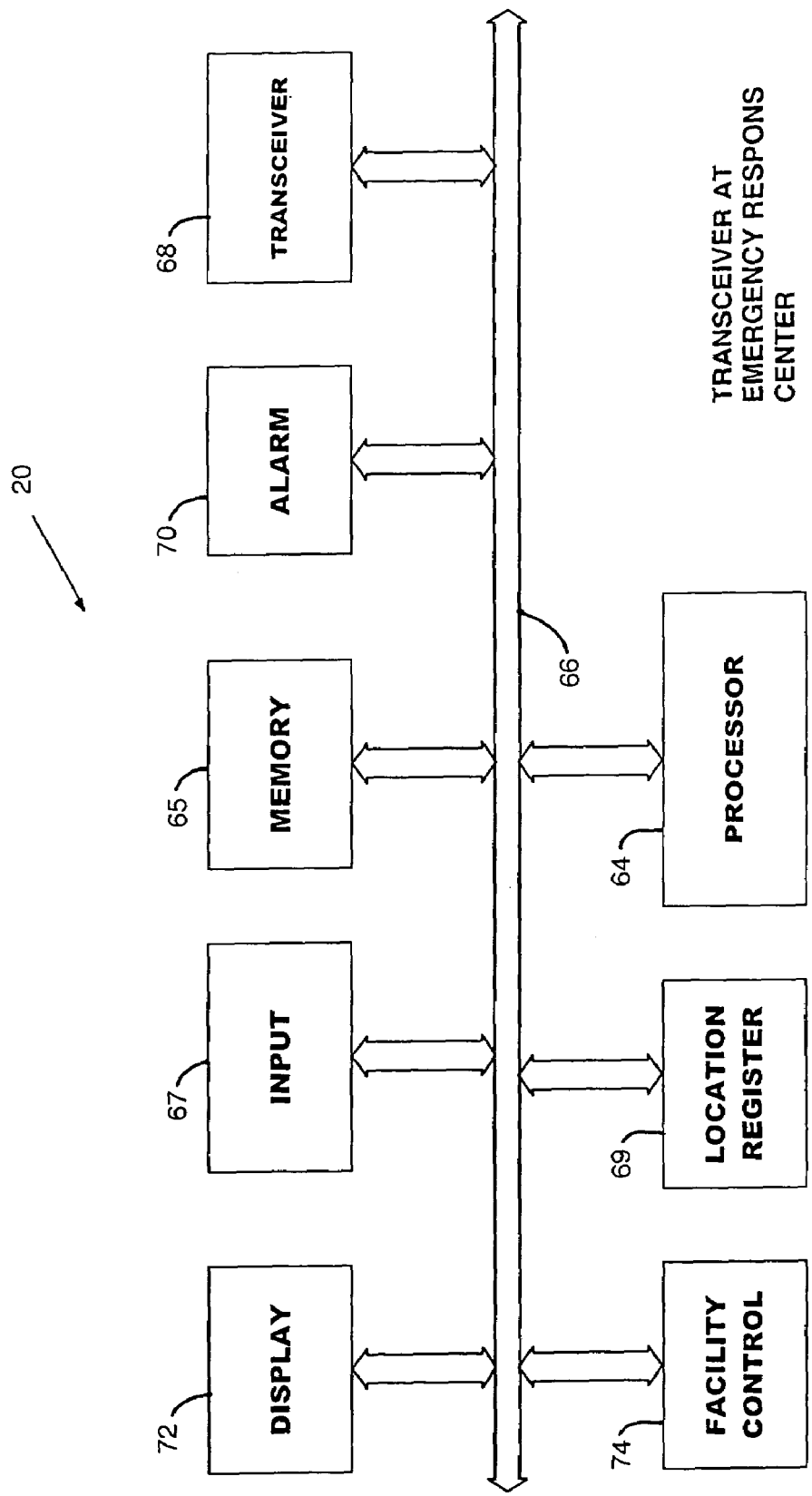
FIG. 4 depicts an exemplary circuit block diagram of a receiver located at an emergency response center to receive medical status and alert information about the patient according to an aspect of the present invention.

FIG. 4 is a circuit block diagram of an exemplary transceiver unit 20 located at an emergency response center or a mobile unit thereof. Transceiver unit 20 comprises a local processor 64 that conveys data over bus 66 with peripheral devices including memory 65, display 72, transceiver 68, alarm 70, I/O interface 67, facility control unit 74, and location register 69. In operation, transceiver 68 receives messages, e.g., data packets, transmitted by the patient's wearable device 10, which messages may be parsed into location, patient ID, and alarm status information and supplied to local memory 65. The patient's location is supplied to a local location register 69. Processor 64 may activate a local alarm 70 and effect display of patient information on a local display 72 useful to emergency response personnel to identify the patient, a need of assistance, and perhaps, the type and extent of assistance needed. I/O interface or input 67 enables a reply transmission to the persona caretaker or patient indicating that "help is on the way." The reply message may be preprogrammed or composed by the emergency response personnel.

In special a case where secure access is required to the patient's home or other facility, control facility 74 of the emergency response unit 20 is operable to implement secure access such as by entering access codes or unlocking an access door 76 of the patient's home 78, as shown in FIG. 5.

Figure 6:
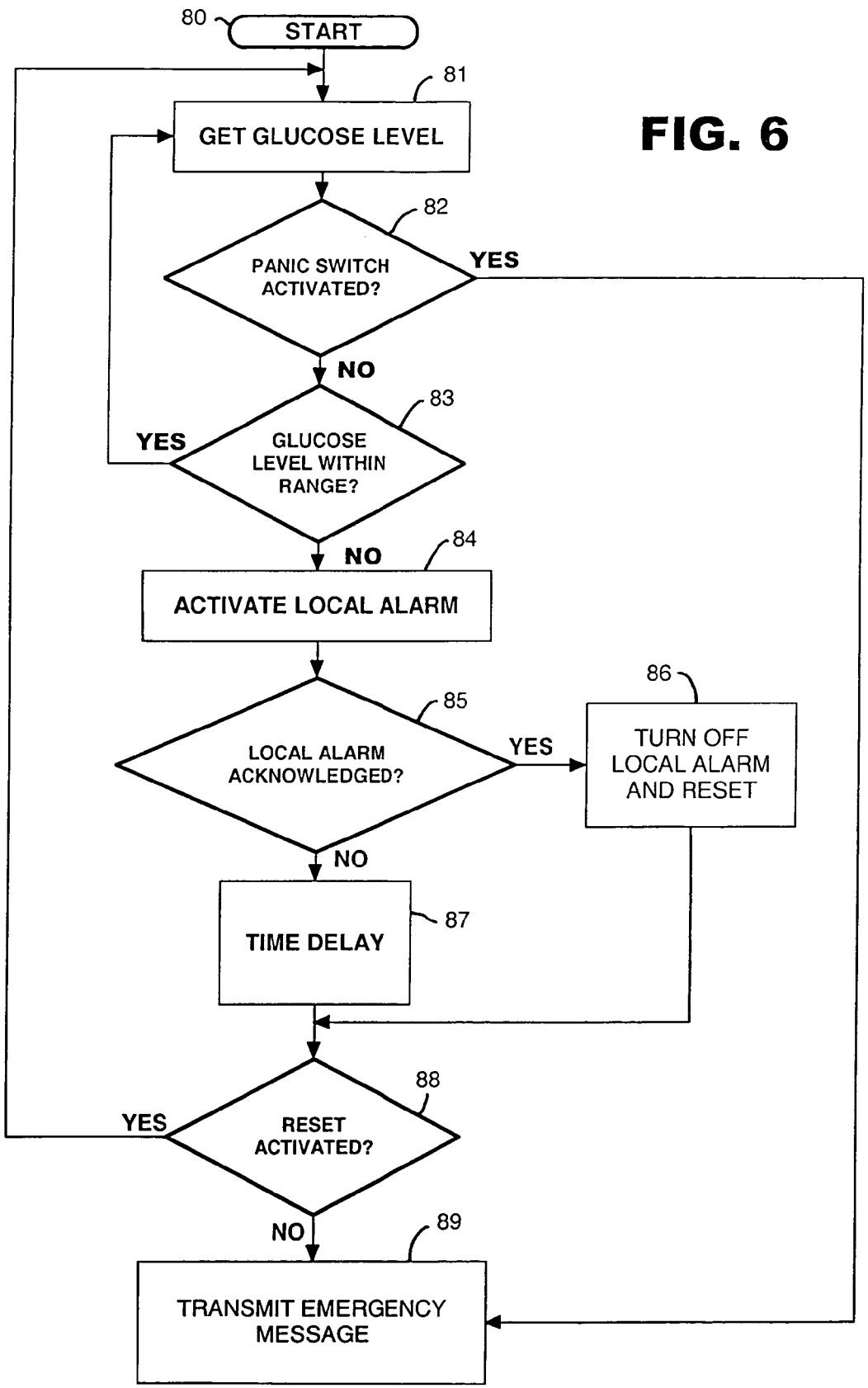
FIG. 6 is a flow chart illustrating an exemplary algorithm or method implemented by a controller of a wearable monitor/transmitter according to an aspect of the present invention.

FIG. 6 is a flow chart illustrating an algorithm implemented by processor 30 (FIG. 2) of the patient's wearable device 10 (FIG. 1). Start step 80 initializes the processor, memory, and registers of device 10, such as by performing diagnostics and self-checks, in a conventional manner. It is assumed the clock 28 (FIG. 2) is properly set, the battery (not shown) holds an adequate charge, the GPS receiver 24 (FIG. 2) is operational, ID register 36 (FIG. 2) is loaded with a patient identifier, the alarms 48 and/or 49 (FIG. 2) is operational, that the glucose sensor 40 (FIG. 2) and transmitter 39 are operational, and that predetermined limit values are entered for high and low glucose levels are properly input and stored in memory. If not, processor 30 (FIG. 2) may prompt the patient either by voice or textual prompts on the display 46 (FIG. 2) to load appropriate data and/or reset the system. Processor 30 effects acquisition of user data using input 38 and display 46 in a conventional manner. Processor 30 may also annunciate a low-battery condition when stored charge falls below a preset level.

Assuming device 10 reaches a normal operating or "green light" state and no system errors are encountered during initialization, step 81 effects acquisition of glucose levels from sensor 40 via buss 34 and stores that information in memory 44. At step 82, processor 30 checks or tests whether the patient has activated the panic switch 42 (FIG. 2) and, if so, immediately jumps to step 89 to transmit an emergency message. As earlier indicated, the emergency message may include patient identification data, a current patient glucose level, date/time-stamped historical glucose levels of the patient, the patient's whereabouts including one of a set of coordinates and an address associated with the coordinates, a nature and/or extent of the emergency, and/or other data useful for emergency response personnel or the patient's personal caretaker.

If, at step 82, processor 30 does not sense activation of panic switch 42, the algorithm proceeds to step 83 to test whether the sensed glucose level lies within proper high and low limits, which may be programmed to correspond to specific hyperglycemia and hypoglycemia conditions of the patient. Such limits may be custom-programmed or predetermined individually for each patient since an alarm condition may differ among diabetic individuals. If, at step 83, a currently detected glucose level lies within the predetermined and proper range, the algorithms loops back to step 81 where a new glucose level is obtained from glucose sensor 40. The periodicity of looping or looping interval may, for example, be set between five and fifteen minutes, more or less, depending on the extent of the patient's monitoring needs and/or the cycle time of glucose sensor 40. In urgent cases, monitoring may occur every minute but in mild case, monitoring may occur every half-hour, hour, or even longer. The periodicity or intervals between monitoring may also be controlled according to historical trend information and/or the proximity of a measured glucose level to an unsafe limit. For example, if processor 30 detects a persistent rise in glucose levels towards a hyperglycemic limit or a persistent decrease in blood glucose level towards a hypoglycemic limit, intervals between measurements or sampling may be shortened, e.g., every minute to every five minutes, more or less. Contrary, if a detected glucose level approaches a mid-point or safe range, measurement intervals may be lengthened.

When, at step 83, processor 30 determines that the currently sensed glucose level lies outside a safe limit or is approaching an unsafe preset limit, step 84 effects activation of local alarm 48 and/or 49 (FIG. 2). At this point, no emergency message is transmitted, but instead, processor 30 provides the patient an opportunity to examine his or her own condition and to take corrective action if necessary. A time delay of thirty to sixty seconds, more or less, after local alarm activation permits the patient to decide whether to turn off the local alarm at step 86 by entering an input at I/O device 38, which also automatically resets the device 10 and proceeds to step 88. Patient input events are monitored by processor 30 and upon detecting a reset, the algorithm loops back to step 81 to restart glucose monitoring. If, at step 88, processor 30 has not detected an acknowledgement after expiration the thirty-to-sixty second time delay at step 87, and the patient has not otherwise manually reset the device 10, the algorithm proceeds to step 89 where processor 30 effects transmission of the emergency message to call for help. The automatic transmission of such message after a pre-set time delay guards the patient against incapacity or unconsciousness, but still enables the patient to cancel the emergency and associated emergency services costs when the matter can be immediately resolved.

Algorithms implemented by the processor 50 (FIG. 3) of the caretaker device 20 and processor 64 (FIG. 4) at the emergency response center are much simpler.

Processor 50 (FIG. 3), for example, monitors incoming messages for an alarm status, which effects activation of local alarm 60. This notifies the caretaker that the patient may need assistance. The caretaker's device 14 may also transmit an acknowledgement message to the patient that "help is on the way" or may elicit a confirmation from emergency response personnel that they received the patient's emergency message and will respond to the patient's need. Memory 58, as previously explained, may store historical glucose level data that is routinely sampled and transmitted by the patient's device. The display 54 and I/O interface 56 may be used to display received data, for setup and control of device 14, or to transmit textual or other information to the patient or emergency response center. Received patient data may include the patient's location.

At the emergency response center, processor 64 (FIG. 4), for example, also monitors incoming messages transmitted by the patient's wearable device 10 and may also activate a local alarm 70 in accordance with the status of an alarm segment of an incoming message. Transceiver 68, display 72, input 67, and alarm 70 operate similarly to corresponding devices of the caretaker's unit 14. Location register 69 records the patient's location to aid emergency response personnel in reaching the patient. In the special case where such personnel is provided with access control to the patient's home or other premises, a facility control unit 74 effects unlocking of an access door specified by the patient. Unlocking may occur automatically upon arrival of the emergency response personnel or access codes may be provided to permit access.

A further embodiment of the invention includes an automatic glucose injection system responsive to a failure of the patient to respond by administering self-treatment when the glucose level detector detects a low blood glucose level. This is especially advantageous for critically afflicted diabetics or where a caretaker or emergency response personnel cannot or will not likely reach the patient before criminality (e.g., patient becoming comatose), which may occur within fifteen to twenty minutes, more or less, in certain cases.

Figure 7:
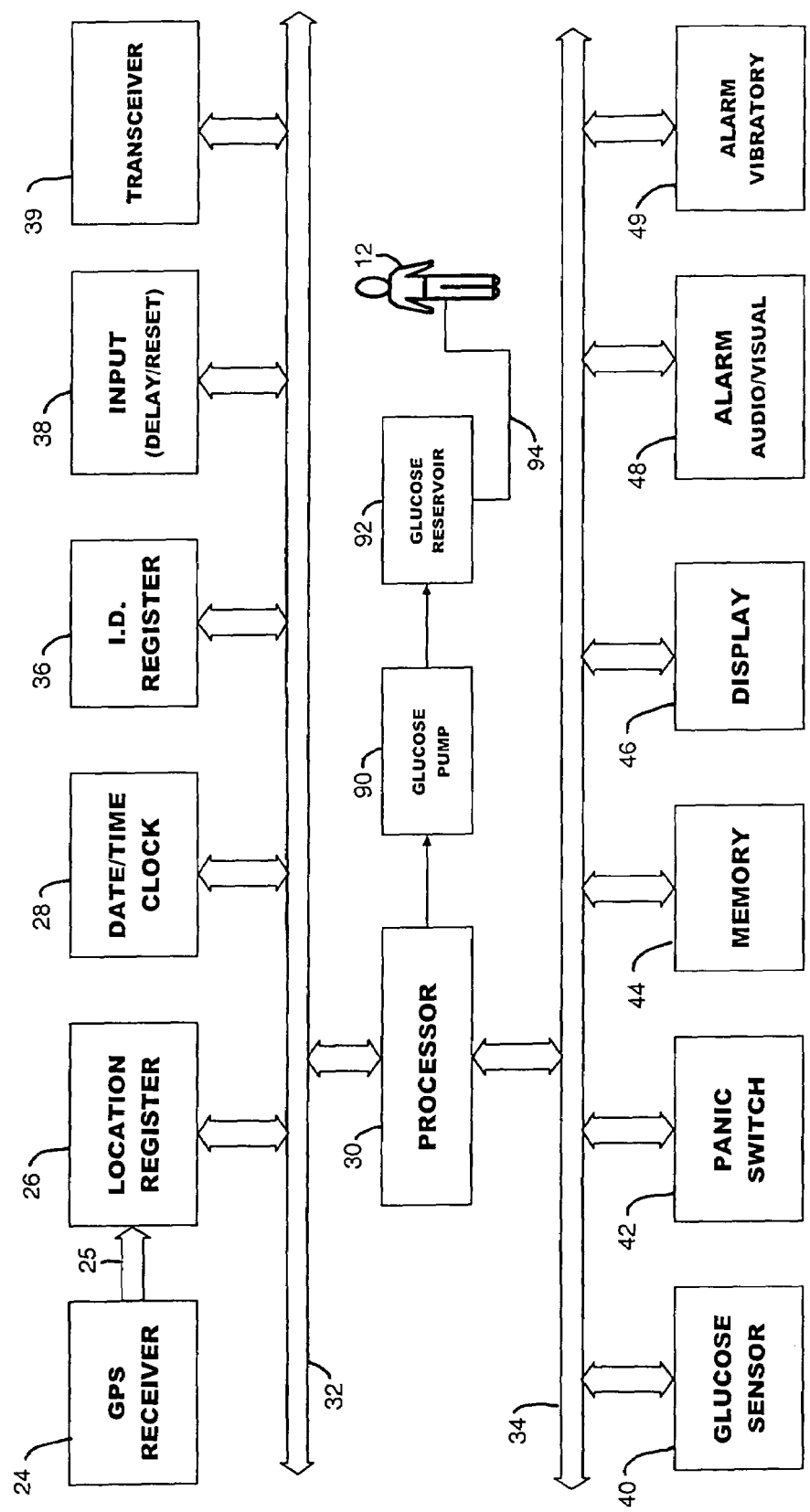
FIG. 7 is a modification of the circuit block diagram of FIG. 2 that includes an automatic glucose injector operative when the patient fails to self-treat a hypoglycemic condition.

FIG. 7 shows a modification of the circuit block diagram of FIG. 2 to achieve the aforementioned goal, which further includes a glucose pump 90 controlled by processor 30 to automatically pump glucose from a reservoir 92 into a limb of patient 12 via an implanted catheter when the patient fails to self-treat a dangerous hypoglycemic condition. The amount of glucose pumped may be metered by processor 30 according to detected blood glucose levels, or the injections may be staggered for repeated, successive injections of glucose according to measured blood glucose levels after each such injection.

The invention is not limited by the illustrative method and apparatus embodiments described above, it being understood that persons having skill in the art may envision further modifications, substitutions, and alterations to the illustrated embodiments without departing from the invention, as defined by the appended claims.

I claim:

1. An emergency medical monitoring and transmission system capable of sending a message to both a personal caretaker and an emergency response center, said system comprising:
   a wearable monitor/transmitter device that includes a glucose level detector to detect a blood glucose level of a patient, a geolocation system that indicates location of said patient, and a communication interface to send a message;
   a processor unit operable with said wearable monitor/transmitter device that collects information produced by said glucose level detector and said geolocation system to determine whereabouts and existence of a hypoglycemic or hyperglycemic condition of said patient, wherein said processor unit effects collection of blood glucose levels at time instances that vary according to proximity of a detected level to an unsafe limit; said processor unit further including program instructions to effect assembly of said message that includes patient identifier data, whereabouts of said patient, and an emergency alert indication; and said processor being further operable to effect activation of said communication interface to transmit said message in response to a hypoglycemic or hyperglycemic condition of said patient;
   a transmission path of said communication interface to send, in response to said emergency alert indication, an emergency message to an emergency response center and to said personal caretaker to simultaneously indicate at at least two locations that the patient requires assistance; and
   a caretaker receiver accessible by a personal caretaker of said patient to receive said message and to produce an alarm indicating that the patient requires assistance in response to receipt of said emergency alert indication.

2. The emergency medical monitoring and transmission system as recited in claim 1, wherein said message includes patient identifier and whereabouts data, said system further comprising an emergency medical response center receiver to receive said message, to produce an alarm, and to display said patient and whereabouts data.

3. The emergency medical monitoring and transmission system as recited in claim 1, wherein said processor unit further includes program instructions to produce and record historical trend information indicating past levels of blood glucose of said patient.

4. The emergency medical monitoring and transmission system as recited in claim 3, wherein said processor unit effects transmission of said historical trend information to at least one of said caretaker receiver and said emergency response center.

5. The emergency medical monitoring and transmission system as recited in claim 3, wherein said communication interface comprises a wireless network interface.

6. The emergency medical monitoring and transmission system as recited in claim 5, wherein said wireless network interface communicates with a network access point of a facility of the patient.

7. The emergency medical monitoring and transmission system as recited in claim 3, further including a panic switch, and said processor unit responds to activation of said panic switch to effect immediate transmission of an emergency message.

8. The emergency medical monitoring and transmission system as recited in claim 7, further including a reset switch, and said processor unit responds to activation of said reset switch to cancel an alarm condition and inhibit transmission of said emergency message.

9. The emergency medical monitoring and transmission system as recited in claim 8, further including a glucose reservoir and pump, and said processor unit effects automatic administration of glucose from said reservoir upon a failure of the patient to acknowledge an alarm condition within a predetermined time period.

10. A portable medical monitoring and transmission system that sends an emergency message to call for assistance, said system comprising:
    a portable monitor/transmitter device including a glucose level detector to detect a blood glucose level of a patient, a patient position monitor that indicates location of said patient, a reservoir of glucose and a pump to administer said glucose to the patient, and a transmitter to send said emergency message;
    a reset switch operative to inhibit said transmitter and to forego administration of said glucose to the patient;
    a processor operable with said portable monitor/transmitter device to effect acquisition of information produced by said glucose level detector and said patient position monitor to determine whereabouts and existence of an unsafe medical condition of said patient, said processor further including program instructions to effect assembly of said emergency message to include patient identifier data, patient position information, and an emergency alert indication to issue a prompt to said patient to self-treat said unsafe condition and, in response to a failure of said patient to acknowledge said prompt within a given time period, to effect activation of said transmitter to transmit said emergency message and activation of said glucose pump to automatically administer glucose to said patient, and in response to an acknowledgement of the prompt by the patient within said given time period, to effect operation of said reset switch to inhibit said transmitter and forego administration of glucose by said glucose pump; and
    a transmission path of said transmitter to send, in response to said emergency alert indication, said emergency message to an emergency response center indicating that the patient requires assistance.

11. The portable medical monitoring and transmission system recited in claim 10, further comprising a caretaker receiver accessible by a personal caretaker to receive said emergency message and, in response to receipt of said emergency alert indication to produce an alarm india that the patient requires assistant.

12. The portable medical monitoring and transmission system recited in claim 10, wherein said portable monitor/transmitter device includes a panic switch to effect immediate transmission of said emergency message.

13. The portable medical monitor and transmission system recited in claim 12, wherein said transmission path includes one of a wireless network, cellular telephone network, Internet, a local computer/telephone modem dialup network.

14. The portable medical monitoring and transmission system recited in claim 12, wherein said portable monitor/transmitter includes one of an audio/video alarm interface and a vibrator, and said processor prompts the patient to perform self-treatment in response to an alarm.

15. The portable medical monitoring and transmission system recited in claim 12, wherein said processor sends said emergency message upon a failure to receive local acknowledgment by said patient within a predetermined time period.

16. The portable medical monitoring and transmission system recited in claim 10, wherein said portable monitor/transmitter includes a reservoir of glucose and a pump to intravenously administer said glucose. and processor automatically activates said glucose pump to treat the patient within a predetermine time after the patient fails to acknowledge and/or perform self-treatment.

17. The portable medical monitoring and transmission system recited in claim 12, wherein said emergency message includes an indication of one or more of blood glucose level, patient identification, medical history, resident address, and emergency contact information.

18. The portable medical monitoring and transmission system recited in claim 17, wherein said emergency message includes secure access codes to allow emergency response personnel to gain access to a residence of the patient.

19. The portable medical monitoring and transmission system recited in claim 11, wherein said caretaker receiver is wearable by said personal caretaker and includes audio/video interface to convey information to the personal caretaker about a condition of the patient 20. The portable medical monitoring and transmission system recited in claim 19, wherein said caretaker receiver includes transmitter to contact patient directly.

21. The portable medical monitoring and transmission system recited in claim 20, wherein said caretaker receiver includes capability to contact emergency response center directly.

22. A method of sending an alert that a diabetic patient needs assistance utilizing a system provided with a reset switch to inhibit sending said alert, said method comprising the steps of:
  detecting a blood glucose level of said patient to produce blood glucose level information,
  determining the location of said patient,
  accessing said blood glucose level information and determining whether said information lies within preset limits corresponding to a hypoglycemic or hyperglycemic condition of said patient,
  in response to said information lying outside said preset limits, prompting the patient to self-treat an unsafe condition,
  upon a failure of the patient to acknowledge said prompting within a given time period,
  (i) automatically treating said patient with an injection of glucose from a wearable reservoir of glucose,
  (ii) assembling an emergency message that identifies said patient, whereabouts of said patient, and an emergency alert indication; and
  (iii) transmitting said emergency message to one of an emergency response center and a personal caretaker to indicate that the patient requires assistance, and
  in response to the patient acknowledging said prompting within a given time period, activating said reset switch to forego said treating and transmitting steps.

* * * * *